United States Patent [19]

Marek

[11] Patent Number: 4,746,452

[45] Date of Patent: May 24, 1988

[54] EASY TO HOLD LUBRICOUS COMPOSITION ARTICLES

[75] Inventor: William E. Marek, Grand Junction, Colo.

[73] Assignee: Christen Charis, N.Y.

[21] Appl. No.: 917,616

[22] Filed: Oct. 10, 1986

[51] Int. Cl.[4] .......................... A61K 7/40; A61K 7/48; A61K 7/50; C11D 17/00

[52] U.S. Cl. .................................... 252/134; 252/174; 252/DIG. 16; D28/8.1; D28/8.2

[58] Field of Search .................. D28/8.1, 8.2; 252/92, 252/134, 174, DIG. 16

[56] References Cited

U.S. PATENT DOCUMENTS

| | | | |
|---|---|---|---|
| D. 16,928 | 10/1886 | Adler | D28/8.1 |
| D. 48,927 | 4/1916 | Bueter | D28/8.1 |
| D. 110,971 | 8/1938 | Lewis | D28/8.1 |
| D. 132,350 | 5/1942 | Stoner | D28/8.1 |
| D. 137,202 | 2/1944 | Scott | D28/8.1 |
| D. 226,038 | 1/1973 | Barere | D28/8.1 |
| D. 247,644 | 3/1978 | Berman | D28/8.1 |
| 268,321 | 11/1882 | Haagen | 252/134 |

FOREIGN PATENT DOCUMENTS

| | | | |
|---|---|---|---|
| 2039787 | 2/1972 | Fed. Rep. of Germany | 252/134 |
| 662971 | 8/1929 | France | 252/92 |
| 1021335 | 2/1953 | France | 252/174 |
| 3601 | of 1891 | United Kingdom | 252/134 |

*Primary Examiner*—Dennis Albrecht
*Attorney Agent, or Firm*—Kane, Dalsimer, Sullivan, Levy, Eisele and Richard

[57] ABSTRACT

Lubricous compositions such as cleansing soaps are fabricated into a geometric shape which facilitates their being hand held while being used. In one embodiment, a bar of soap is provided having finger-gripping surfaces both top and bottom as well as around the bar periphery.

3 Claims, 1 Drawing Sheet

EASY TO HOLD LUBRICOUS COMPOSITION ARTICLES

BACKGROUND OF THE INVENTION

1. Field of the Invention

The invention relates to articles manufactured of lubricous compositions such as cleansing soaps, employed to apply the composition to a surface by hand.

2. Brief Description of the Prior Art

Representative of articles manufactured for hand application of lubricous compositions are bars of cleansing soaps, sticks of deodorant gels, grease "pencils" and the like. Such articles are well known. Equally well known is the fact that such articles, unless associated with a separate means for gripping, are difficult to hold during use because of the inherent low coefficient of friction characteristic of the specific composition.

The present invention solves the difficulty of holding such articles while using them, without the need for adding a separate gripping means such as a handle, container or special applicator. By fabricating the article in a special configuration, holding of the article in the human hand is facilitated.

SUMMARY OF THE INVENTION

The invention comprises an article of manufacture, useful for the application of a lubricous composition, which comprises;

a body adapted by size and configuration to be hand-held and fabricated from a lubricous composition, said body having (a) a first surface defined by a first, outer peripheral boundary and having (i) a first peripheral margin zone extending inwardly of the peripheral margin; and (ii) a first center zone spaced inwardly from the peripheral boundary and defined on its outer perimeter by the peripheral margin;

said first center zone being elevated with respect to the peripheral margin zone;

said peripheral margin zone being concave when viewed in cross-section along a line transverse to the axis of the peripheral margin running parallel to the first outer boundary;

said concavity having an arc such that the first digit of an operator's finger may be inserted into the peripheral margin zone to engage the article;

(b) a second surface defined by a second, outer peripheral boundary and having (i) a second peripheral margin zone extending inwardly of the second, outer peripheral boundary; and (ii) a second center zone spaced inwardly from the second peripheral boundary and defined on its outer perimeter by the second peripheral margin;

said second center zone being elevated with respect to the second peripheral margin zone;

said second peripheral margin zone being concave when viewed in cross-section along a line transverse to the axis of the peripheral margin running parallel to the second outer boundary;

said concavity of the second peripheral margin having an arc such that the first digit of an operator's finger may be inserted into the second peripheral margin zone to engage the article in a finger hold; and (c) a third surface extending between and defined by the first and the second peripheral boundaries together, said third surface serving to space the first peripheral boundary from the second peripheral boundary;

said first and said second peripheral boundary being substantially parallel and co-extensive, each with the other;

said first and said second peripheral boundary together, when viewed along a line transverse to their parallel axis, presenting a closed serpentine line of a plurality of concavities and a plurality of convexities, said concavities having a sufficient arc to receive a portion of an operator's finger in the concavity, in a finger hold.

The articles of the invention are useful for applying lubricants, cleansing soaps and like compositions ordinarily difficult to hold, due to the low coefficient of friction associated with bodies fabricated from such compositions.

DETAILED DESCRIPTION OF THE PREFERRED EMBODIMENTS OF THE INVENTION

Those skilled in the art will gain a complete appreciation of the invention from the following description of the preferred embodiments of the invention when read in conjunction with a viewing of the accompanying drawings of FIGS. 1–4.

Figure 1:
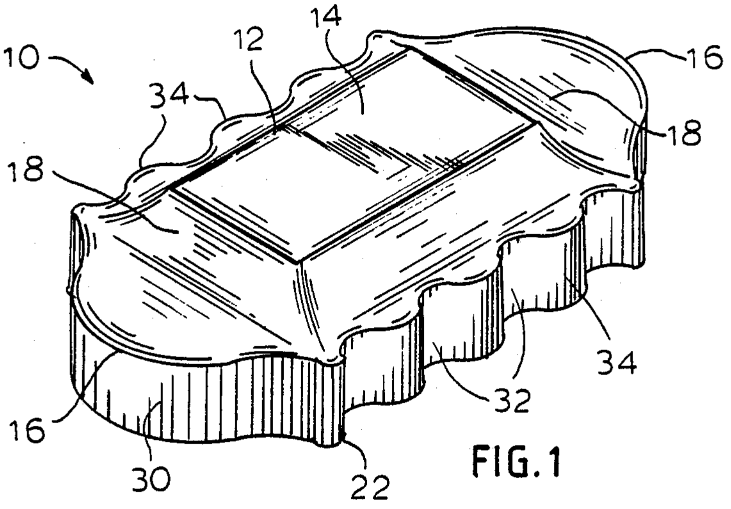
FIG. 1 is a view-in-perspective of an embodiment article of the invention.
Figure 2:
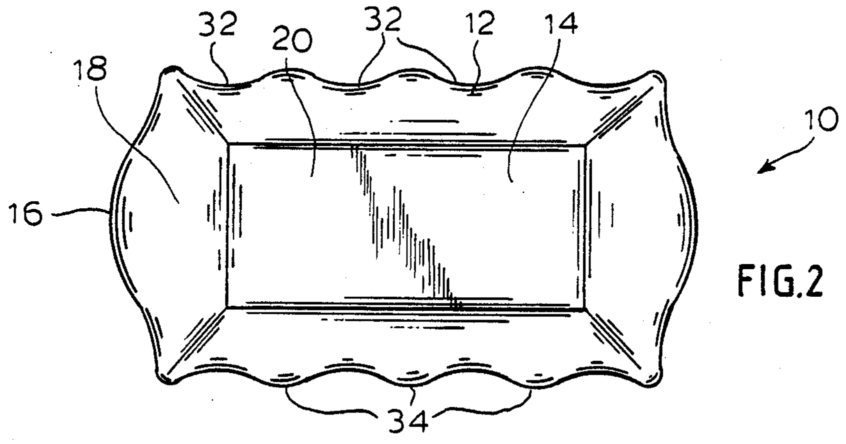
FIG. 2 is a top elevation of the article of FIG. 1.

Referring first to FIG. 1, a perspective view of an article 10 of the invention is shown. The article 10 for purposes of illustration is a cleansing soap composition which is lubricous in nature, particularly when wet. The article 10 may be of a size and configuration adapted to be hand-held in the human hand. A typical and illustrative size would be a length of approximately 4 inches, a width of approximately 2 inches and a thickness of approximately 1 or 2 inches. The shape of the article 10 is not important and it may be oval, rectangular, round, square, cylindrical, etc. The article 10 comprises a body 12 having a first surface 14 defined by a first, outer peripheral boundary 16 and having a first peripheral margin zone 18 extending inwardly of the peripheral boundary 16 and a first center zone 20 spaced inwardly from the peripheral boundary line 16 and defined on its outer perimeter by the peripheral margin zone 18. The first center zone 20 is elevated with respect to the peripheral margin zone 18. The peripheral margin zone 18 is concave when viewed in cross-section (see FIGS. 3 and 4) along a line transverse to the axis of the peripheral margin zone 18, running parallel to the first outer boundary 16. This concavity has an arc such that the first digit of an operator's finger may be inserted into the peripheral margin zone 18 to engage the article 10 in a single hold.

A second surface (not seen in FIG. 1) is identical to that of the first surface and is defined by a second, outer peripheral boundary line 22. Like the first surface, the second surface includes a second peripheral margin zone 24 (see FIG. 3) extending inwardly of the second, outer peripheral boundary line 22. A second center zone 26 (see FIG. 3) is spaced inwardly from the second peripheral boundary line 22 and is defined on its outer perimeter by the second peripheral margin zone 24. The second center zone 26 is elevated with respect to the second peripheral margin zone 24 as clearly shown in FIG. 3. The second peripheral margin zone 24 is concave when viewed in cross-section along the line transverse to the axis of the peripheral margin running parallel to the second, outer boundary; see FIGS. 3 and 4. The concavity of the second peripheral margin zone 24 has an arc such that the first digit of an operator's finger may be inserted into the second peripheral margin zone to engage the article 10 in a finger hold. A third surface 30 extends between and is defined by the first and second peripheral boundary lines 16, 22. The third surface 30 serves to space the first peripheral boundary line 16 from the second peripheral boundary line 22. The first and second peripheral boundary lines 16, 22 are substantially parallel and co-extensive each with the other. The first and second peripheral boundary lines 16, 22 together, when viewed along a line transverse to their parallel axis, presents a closed, serpentine line of a plurality of concavities 32 and a plurality of convexities 34. The concavities have a sufficient arc to receive a portion of an operator's finger in the concavity, to establish a finger hold. The concavities 32 alternate with the convexities 34. The concavities 32 and convexities 34 are preferably uniformly distributed over the entire surface 30. However, this is not a necessity and the concavities 32 and convexities 34 need not be uniform in size, spacing or location.

In operation, the user or operator of article 10 will engage a concavity 32 or a plurality of concavities 32 with portions of fingers on a single hand. The concavity 18 may also be engaged by the first digit of any finger. With the hand partially closed, the article 10 may be held in the palm of the hand, firmly gripped by fingers. An advantage of the article 10 of the invention resides in the fact that regardless of of positioning of the article 10 within the palm of the hand, the fingers can engage one or more of the concavities 32, 18 to firmly hold article 10 in the palm of the hand. Even when the lubricous composition is wetted or partially wetted, a firm engagement may be had to prevent slippage and loss of the article 10 from the operator's hand during use. The article 10 may be said to be "slip-proof" regardless of how it lies within the palm of the hand.

Figure 3:
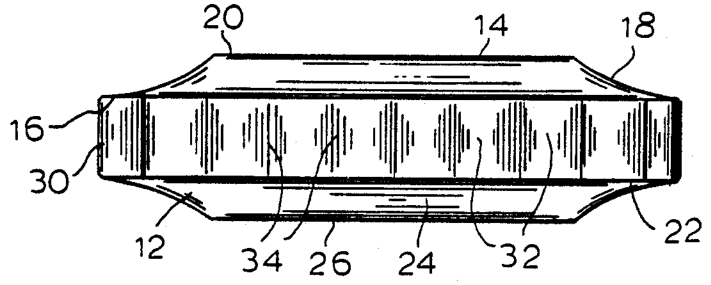
FIG. 3 is a side elevation of the article of FIG. 1.
Figure 4:
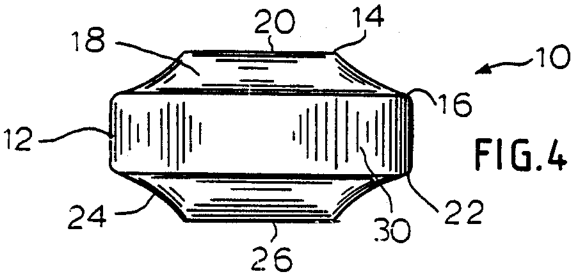
FIG. 4 is an end view of the article of FIG. 1.

What is claimed is:

1. An article of manufacture, useful for the application of a lubricous composition, which comprises;

a body, adapted by size and configuration to be hand-held and fabricated from a lubricous composition, said body having (a) a first surface defined by a first, outer peripheral boundary and having (i) a first peripheral margin zone extending inwardly of the peripheral margin; and (ii) a first center zone spaced inwardly from the peripheral boundary and defined on its outer perimeter by the peripheral margin;

said first center zone being elevated with respect to the peripheral margin zone;

said peripheral margin zone being concave when viewed in cross-section along a line transverse to the axis of the peripheral margin running parallel to the first outer boundary;

said concavity having an arc such that the first digit of an operator's finger may be inserted into the peripheral margin zone to engage the article;

(b) a second surface defined by a second, outer peripheral boundary having (i) a second peripheral margin zone extending inwardly of the second, outer peripheral boundary; and (ii) a second center zone spaced inwardly from the second peripheral boundary and defined on its outer perimeter by the second peripheral margin;

said second center zone being elevated with respect to the second peripheral margin zone;

said second peripheral margin zone being concave when viewed in cross-section along a line transverse to the axis of the peripheral margin running parallel to the second outer boundary;

said concavity of the second peripheral margin having an arc such that the first digit of an operator's finger may be inserted into the second peripheral margin zone to engage the article in a finger hold;

said first and second peripheral margin zones being endless grooves; of the first and second center zones being substantially flat; and (c) a third surface extending between and defined by the first and the second peripheral boundaries together, said third surface serving to space the first peripheral boundary from the second peripheral boundary;

said first and said second peripheral boundary being substantially parallel and co-extensive, each with the other;

said first and said second peripheral boundary together, when viewed along a line transverse to their parallel axis, presenting a closed serpentine line of a plurality of concavities and a plurality of convexities, both uniformly distributed over the entire third surface, said concavites having a sufficient arc to receive a portion of an operator's finger in the concavity, in a finger hold, said article having the configuration substantially as shown in FIGS. 1 and 3.

2. The article of claim 1 wherein the lubricous composition is a cleansing soap.

3. The article of claim 1 wherein the plurality of concavities and the plurality of convexities are uniformly spaced apart, concavities alternating with convexities along the serpentine line.

* * * * *